United States Patent [19]

Masuda et al.

[11] Patent Number: 5,994,322
[45] Date of Patent: Nov. 30, 1999

[54] COMPOSITIONS FOR PREVENTING DEMENTIA

[75] Inventors: Yasunobu Masuda; Toyohiko Kokubu; Norimitsu Yamagata, all of Hino, Japan

[73] Assignee: Kewpie Kabusiki Kaisya, Japan

[21] Appl. No.: 08/631,883

[22] Filed: Apr. 16, 1996

Related U.S. Application Data

[63] Continuation of application No. 08/245,858, May 19, 1994, abandoned, which is a continuation of application No. 07/742,637, Aug. 8, 1991, abandoned.

[30] Foreign Application Priority Data

Aug. 8, 1990 [JP] Japan ................................ 2-208172

[51] Int. Cl.$^6$ ...................... A61K 31/715; A61K 31/685; A61K 35/54
[52] U.S. Cl. ........................... 514/52; 514/78; 514/185; 514/186; 514/492; 424/581
[58] Field of Search .......................... 514/78, 185, 186, 514/52, 492; 424/581

[56] References Cited

U.S. PATENT DOCUMENTS 4,657,866 4/1987 Kumar ............................... 435/240.31
5,000,975 3/1991 Tomarelli .............................. 426/602

FOREIGN PATENT DOCUMENTS 274348 7/1988 European Pat. Off. .
58-216122 12/1983 Japan .

OTHER PUBLICATIONS

Chemical Abstracts 100: 91421K. 1984.
Chemical Abstracts 109: 127547h. 1988.
Remington's Pharmaceutical Sciences, 15$^{th}$ edition, Easton (PA), Mack Publishing Company, 1975. pp. 425, 955–957 and 1452–1453.
Gillin et al., "Effects of lecithin on memory . . . " Adv. Behav. Biol., vol. 25, 1981, pp. 937–945.
Sorgatz et al., "The influence of lecithin on the parameters of learning . . . " FORTschritte der Medizin, vol. 34, 1986, pp. 643–646.
Chemical Abstracts 106: 43882 p. 1987.
Ezer, E. et al. "Tape test as a simple new method . . . " Psychopharmacology, 1976, vol. 48(1), pp. 97–99.
Pomara et al., "A Dose–Response Study of Lecithin in the treatment of Alzheimer's Disease," Aging, vol. 19 (Alzheimer's Disease: Report of Progress), pp. 379–383 (1982).
Wyngaarden, James B. et al. (eds.), Cecil Textbook of Medicine, 19$^{th}$ ed., Philadelphia, W.B. Saunders Co., pp. 2075–2079, (1992).

*Primary Examiner*—John Pak
*Attorney, Agent, or Firm*—Bierman, Muserlian and Lucas

[57] ABSTRACT

Compositions for preventing or treating memory loss in the brain, comprising an effective amount of a mixture of lecithin and vitamin $B_{12}$.

3 Claims, No Drawings

COMPOSITIONS FOR PREVENTING DEMENTIA

This application is a continuation of application Ser. Nos. 245,858 filed May 19, 1994, now abandoned, which is a continuation of 07/742,637, filed Aug. 8, now abandoned.

FIELD OF THE INVENTION

This invention relates to a novel health composition.

BACKGROUND OF THE INVENTION

Recently, in order to prevent learning disability and memory power from deteriorating or to heal clinical dementia, research into the substances and compositions which act to improve or enhance functions of the brain is being pushed forward.

Among these, lecithin has begun to be intensively studied because it occurs widely in the natural world, has almost no side effects when administrated, and is considered to be effective for improving the functions of brain particularly, cholinergic function. It has been reflected that administration of lecithin increases concentration of acetylcholine in the brain, which is said to intermediate transmission of information.

However, since administration of lecithin induces only a very slight increase in concentration of acetylcholine in the brain, and its improvement effect is not conspicuous, a substance for improving the function of the brain which provides a high effect to improve or enhance the function of the brain is in demand.

In view of such circumstances, it is a primary object of the present invention to provide a composition for improving the function of the brain (hereinafter referred to as "brain health composition") which has a high effect to improve or enhance the function of the brain.

SUMMARY OF THE INVENTION

In accordance with the present invention which attains the above object, there is provided a brain health composition comprising lecithin and vitamin $B_{12}$.

In the present invention, lecithin refers to phosphatidylcholine (including lyso compound) alone, or mixtures of phosphatidylcholine and phospholipid (including lyso compound) other than phosphatidylcholine or neutral lipid, which include crude lecithin such as crude egg yolk lecithin or crude soybean lecithin, lecithin with high phosphatidylcholine content, obtained by purifying crude lecithin, phosphatidylcholine of 100% purity, or the like.

Vitamin $B_{12}$ refers to one which comprises porphyrin-like corrin ring containing cobalt, and one which comprises an imidazole group is especially preferable. Specifically, vitamin $B_{12}$ includes cyanocobalamine, hydroxocobalamine, aquocobalamine, nitrilecobalamine. 5'-deoxyadenosylcobalamine, methylcobalamine and so on.

Furthermore, the brain health composition refers to foods, oral pharmaceuticals, injection pharmaceuticals, or substances which can be used as raw materials thereof.

To obtain the brain health composition according to the present invention, lecithin and vitamin $B_{12}$ as raw materials are to be prepared. Commercial products of these raw materials may be used.

The brain health composition of the present invention can be obtained by mixing lecithin and vitamin $B_{12}$ prepared above as raw materials, and, if necessary, appropriate amounts of other raw materials (food materials, pharmaceutical materials).

For example, commercial egg yolk lecithin (liquid) and vitamin $B_{12}$ (powder) can be mixed to obtain a liquid composition. Commercial soybean lecithin (powder) and vitamin $B_{12}$ can be mixed to obtain a powder composition. Furthermore, the powder composition can be mixed with a solidifying agent such as thick malt syrup and molded to obtain a tablet-formed composition. The thus obtained composition can be taken in as is or mixed with foods.

Furthermore, a starch-based raw material such as wheat flour, a sweetener such as sugar, and a gelling agent such as carrageenin may be added to lecithin and vitamin $B_{12}$, and the mixture can be used to make foods by conventional methods to obtain edible compositions such as liquid foods, confectionery, jelly, and the like.

Physiological saline, lecithin, and vitamin $B_{12}$ can be mixed and emulsified by a conventional method known in the art to obtain a composition for peritoneal administration or intravenous injection.

The brain health composition according to the present invention preferably contains lecithin in an amount of 1% by weight or more, more preferably 3% by weight or more, converted to pure phosphatidyloholine equivalent. Weight ratio of lecithin and vitamin $B_{12}$ a in the composition is preferably such that 1 to 50 parts by weight of the former, converted to pure phosphatidylcholine equivalent, is used with $1 \times 10^{-6}$ to $1 \times 10^{-4}$ parts by weight of the latter. Showing an example of actual intake, when pure phosphatidylcholine as lecithin is used, 5 to 50 g of lecithin and 1 to 100 μg of vitamin $B_{12}$ are preferably used per daily intake (for male adult). When the content of each material is smaller than the ranges, effects to improve or enhance the function of brain tend to be lost, and when each content is excessive, extra ingredients do not transfer to the brain and tend to be wasted.

As shown in the Test Examples described later, the brain health composition of the present invention has enhanced effects on the function of the brain compared to the intake of lecithin alone or vitamin $B_{12}$ alone.

Although the principle of the action has yet to be investigated, it is considered that intake of lecithin and vitamin $B_{12}$ promotes intaking photopholipid including Phosphatidylcholine into the brain, enhances the acetylcholine concentration at the cerebral nerve terminal, and vitamin $B_{12}$ influences the acetylcholine synthesis.

Since the brain health composition of the present invention comprises lecithin and vitamin $B_{12}$, intake of the composition can enhance the effect for improving leaning ability even further, presumably by activating the acetylcholine synthesis at the nerve terminal in the brain.

Therefore, the brain health composition of the present invention is suitable as raw materials of foodstuffs and as pharmaceuticals with the aim of healing or preventing clinical dementia.

DESCRIPTION OF THE PREFERRED EMBODIMENTS

EXAMPLE 1

5 kg of soybean salad oil, 3 kg of egg yolk lecithin [brandname "PL-100LE", made by Kewpie K.K.: containing 88% of phosphatidylcholine (hereinafter referred to as "PC")], and 1 mg of vitamin $B_{12}$ ("VITAMIN $B_{12}$", made by Sigma Corp.) were homogeneously mixed.

Separately, 60% (% by weight unless otherwise noted) gelatin, 30% glycerin, and 10% clean water were uniformly mixed and formed into a film, 800 mg each of the mixture was injected into an injection--molded capsule-formed container having a volume corresponding to 800 mg of the mixture, and the opening of the container for the injection was sealed by heat to obtain 9,900 capsules of a brain health composition.

The capsules were administered as a dementia healing drug to a dementia patient at a rate of 10 capsules per day.

EXAMPLE 2

The following raw materials were used:

| Soybean salad oil | 7 kg |
| Liquid egg yolk | 3 kg |
| Soybean milk | 39 kg |
| Milk | 39 kg |
| Nonfat milk powder | 5 kg |
| Sugar | 2 kg |
| Soybean lecithin (PC content 80%) | 5 kg |
| Vitamin $B_{12}$ (methylcobalamine) | 1 mg |

These raw materials were mixed by a mixer, emulsified by a homogenizer at 200 kg/cm², and 200 g each of the resulting emulsion were charged and sealed in cane, which were retort sterilized at 116° C. for 30 minutes, and cooled to obtain 450 cans of a brain health composition (liquid food).

This can as a memory power keeping agent was administrated to 30 persons of old age at a rate of 1 can/day.

TEST EXAMPLES

Tests were conducted using 11-week old male Wister rats under the following conditions.

(Breeding method)

The rats were bred under the same environmental conditions with varied diets over the experimental period.

As a common diet, a 20% casein diet was prepared which was adjusted so that it had no adverse effects on the growth.

Using a spaced feeding method, 15 g of the diet was fed within 4 hours at a predetermined time every day, with water fed freely.

(Method for causing memory keeping impairment)

Ibotenic acid made by Sigma Corp. was dissolved in a phosphate-buffered saline solution to obtain a 30 n mol/µl ibotenic acid solution A microsyringe was inserted into the medial septal area (A53, LO.0, HO.5, according to the atlas of König & Klippol) of the fixed brain of an anesthetized rat, and 0.6 µl of the ibotenic acid solution was injected over a period of 5 minutes. After the infusion, the microsyringe remained in place for 5 minutes to protect against a backflow, and was removed to prepare a memory-impaired rat.

(Learning)

Acquisition:

A subject of water maze was used as the training for learning 14 days after the surgery mentioned above.

An apparatus for the subject of water maze comprised a water tank (circular tank) of 120 cm in diameter and 40 cm in height, filled with 21° C. water to a depth of 25 cm, and a place of refuge with a surface of 10 cm in both length and width located at a depth of 1 cm from the water surface. Granular foamed polystyrene pieces were floated on the water surface so that the rat cannot see the place of refuge.

On the edge of the water tank, 4 points, east, west, south, and north, were determined to divide the water surface into 4 sections. Around the apparatus, there were objects which could be visible hints for the rat such as researchers and fluorescent lamps for lighting, which were kept unchanged throughout the experiment.

In the training for learning, the rat was placed in the water tank, and the act of the rat until it reached the place of refuge was set as one cycle. 4 cycles were conducted per day at intervals of at least 10 minutes.

Retention:

The place of refuge was removed from the water maze problem apparatus, and the time was measured for which the rat stayed at the place where the refuge was present, during a period of 60 seconds after the rat was put in the water tank.

TEST EXAMPLE 1

20 memory-impaired rats, and 20 control rats subjected to the same treatment except that they were not injected with ibotenic acid, were used for the test. These rats were bred for 17 days with only the common diet.

Of the 17 days, the training for learning was performed for three days from the 14th day to the 16 the day, and the confirmation test of memory keeping power was performed on the 17th day. The results are shown in Table 1.

TABLE 1

| Sample | Time (second) |
| --- | --- |
| Memory keeping impaired rat | 14 |
| Control rat | 27 |

Figures in the table are the average of 20 rats of the time for which they stayed at the place of refuge, and the greater number indicates the better memory keeping power.

From Table 1, it is confirmed that a memory impairment is caused by injecting ibotenic acid into the medial septal area.

Test Example 2

80 memory keeping impaired rate were divided into 4 groups of 20 rats for different types of diet, and tested as in Test Example 1. The results are shown in Table 2.

Group A: Fed with a diet comprising 14.2 g of the common diet mixed with 0.8 g of egg yolk lecithin ("PL-100LE", made by Kewpie K.K.), and a solution (3.5 µg ml) of vitamin $B_{12}$ (cyanocobalamine) dissolved in distilled water was administrated using a catheter at a rate of 25 µg of vitamin $B_{12}$/1 kg of rat weight of vitamin $B_{12}$.

Group B: Fed with the common diet only.

Group C; Fed with the same diet as Group A (lecithin administrated).

Group D: Fed with the common diet, and administrated with vitamin B12 under the same condition as Group A.

TABLE 2

| Sample | Time (second) |
| --- | --- |
| Group A (present invention) | 20 |
| Group B (unadministrated) | 14 |
| Group C (lecithin) | 18 |
| Group D (vitamin $B_{12}$) | 15 |

Figures in the table are average of 20 rats of the time for which they stayed at the place of refuge, and the greater number indicates the better memory keepin g power.

It can be seen from Table 2 that the memory keeping power is improved by administrating both lecithin and vitamin $B_{12}$.

Also, when the rat was fed with a diet mixed with egg yolk lecithin and vitamin $B_{12}$, a similar result was obtained as with Group A of Test Example 2 in terms of the memory keeping power.

What is claimed is:

1. A composition for improving memory retention in a warm-blooded animal consisting essentially of 1 to 50 parts by weight of lecithin and $1\times10^{-6}$ to $1\times10^{-4}$ parts by weight of vitamin $B_{12}$, said lecithin being calculated as pure phosphatidyl choline equivalent and an inert pharmaceutical carrier, wherein the concentration and amount of lecithin and vitamin $B_{12}$ in the composition are effective for providing greater memory retention in said warm-blooded animal than the individual concentration and amount of lecithin or vitamin $B_{12}$ alone.

2. The compositions of claim 1 wherein said lecithin is derived from egg yolk.

3. A method for improving memory retention in warm-blooded animals comprising administering to warm-blooded animals an amount of the composition of claim 1 sufficient to improve memory retention brain functions.

* * * * *